United States Patent [19]

Sutton

[11] Patent Number: 4,652,823
[45] Date of Patent: Mar. 24, 1987

[54] APPARATUS FOR AND METHOD OF MONITORING THE CORROSION IN ELECTRICAL POWER CABLES BY MEASURING THE VARIATION IN INDUCED EDDY CURRENTS

[75] Inventor: John Sutton, Mid Holmwood, Nr Dorking, United Kingdom

[73] Assignee: Central Electricity Generating Board, England

[21] Appl. No.: 612,818

[22] Filed: May 22, 1984

[30] Foreign Application Priority Data

May 23, 1983 [GB] United Kingdom ............... 8314220

[51] Int. Cl.$^4$ ............... G01N 27/90; G01R 33/12
[52] U.S. Cl. .................... 324/240; 324/233; 324/262
[58] Field of Search ............... 324/239–243, 324/260–262, 228–238; 336/20

[56] References Cited

U.S. PATENT DOCUMENTS

| 2806992 | 9/1957 | Foerster . | |
|---|---|---|---|
| 3,281,668 | 10/1966 | Rosner et al. | 324/239 X |
| 3,731,184 | 5/1973 | Goldberg et al. | 324/239 |
| 4,292,589 | 9/1981 | Bonner | 324/221 |
| 4,335,352 | 6/1982 | Stephen | 324/239 X |
| 4,388,593 | 6/1983 | Mittleman | 324/262 |
| 4,495,465 | 1/1985 | Tomaiuolo et al. | 324/239 X |
| 4,546,316 | 10/1985 | Lang | 324/240 X |

FOREIGN PATENT DOCUMENTS

| 0068503 | 1/1983 | European Pat. Off. . | |
|---|---|---|---|
| 0063755 | 5/1980 | Japan | 324/238 |
| 63757 | 5/1980 | Japan | 324/238 |
| 71943 | 5/1980 | Japan | 324/238 |
| 881495 | 11/1961 | United Kingdom . | |
| 1458792 | 12/1976 | United Kingdom . | |
| 1484696 | 9/1977 | United Kingdom . | |
| 1603578 | 11/1981 | United Kingdom . | |
| 2124778 | 2/1984 | United Kingdom | 324/229 |

OTHER PUBLICATIONS

"New Method for Steel Cable Testing Developed at NTH", Berqverks-Nytt (Norwegiar Publication), 7-8/1969, pp. 13-17.

Primary Examiner—Reinhard J. Eisenzopf
Assistant Examiner—Warren S. Edmonds
Attorney, Agent, or Firm—Beveridge, De Grandi & Weilacher

[57] ABSTRACT

A metal cable corrosion monitor comprises a sensing head (14) located about a multi strand cable (1). The sensing head includes a field windings (3) for applying a magnetic field coaxially to a portion of the cable to be monitored. A pick-up coil (2) encircles the portion and detects magnetic flux parallel with the cable and linking with the area of the pick-up coil. The signals from the pick-up coil are processed by a high gain amplifier (8) and phase sensitive detectors (7) and (6), the former phase sensitive detector producing an output in phase with the field winding driving frequency and the latter phase sensitive detector producing a quadruture output relative to the field winding driving frequency. By observation of the amplitude and the phase output parameters it is possible to detect corrosion of a single or multi strand cable. A particular format of field winding is disclosed whereby the effects of induced inter strand currents can be reduced.

10 Claims, 6 Drawing Figures

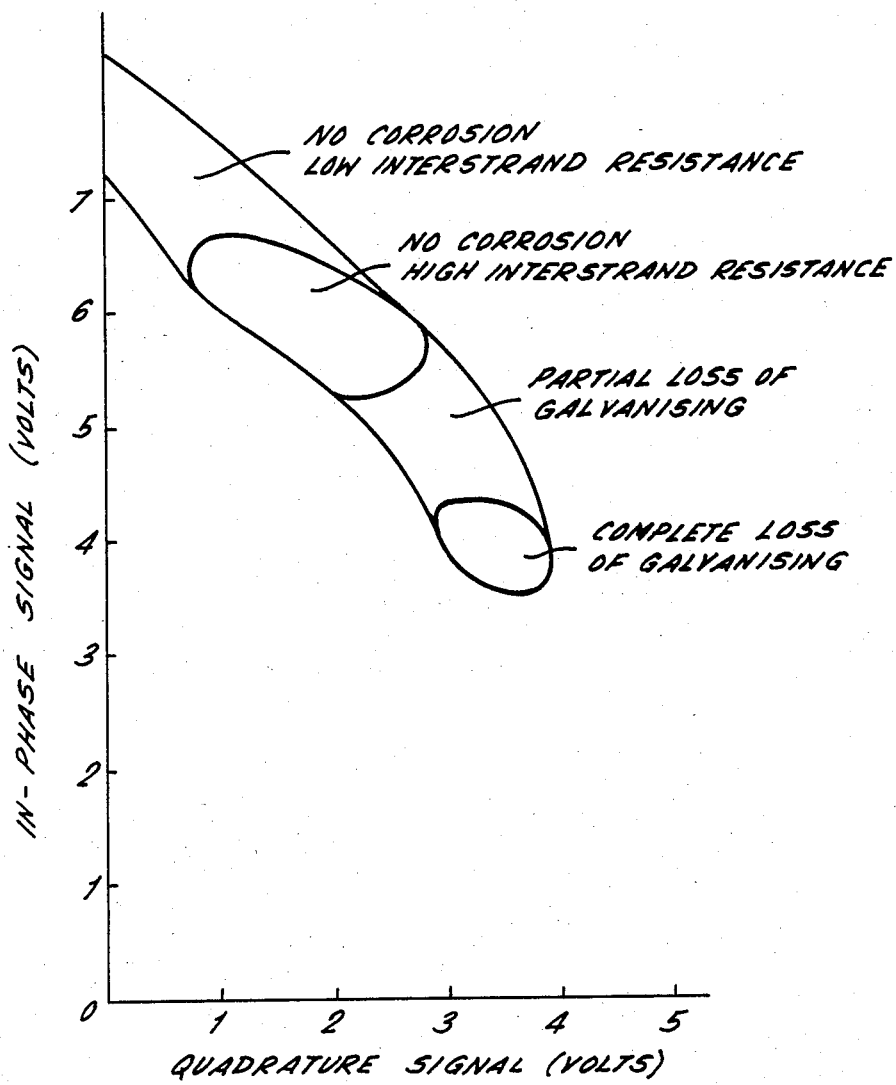
FIG. 3. RESPONSE CHART FOR ZEBRA CONDUCTOR.

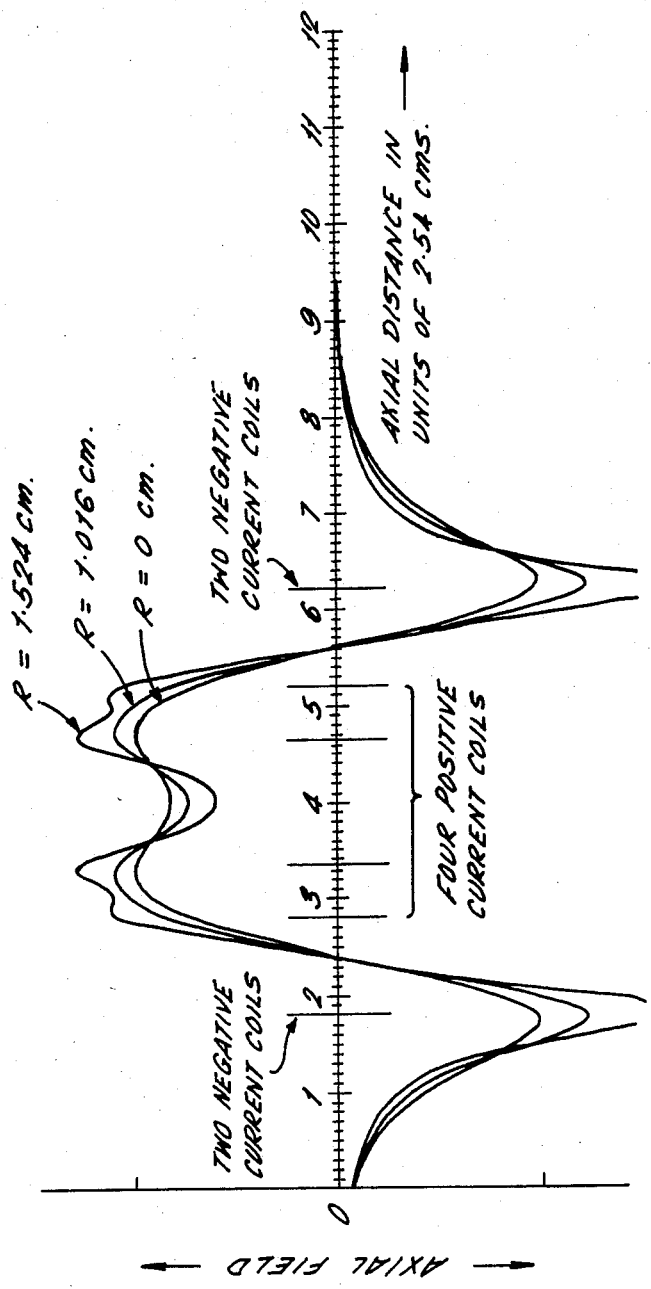
FIG. 4. COMPUTED AXIAL MAGNETIC FIELDS FOR SENSING HEADS.

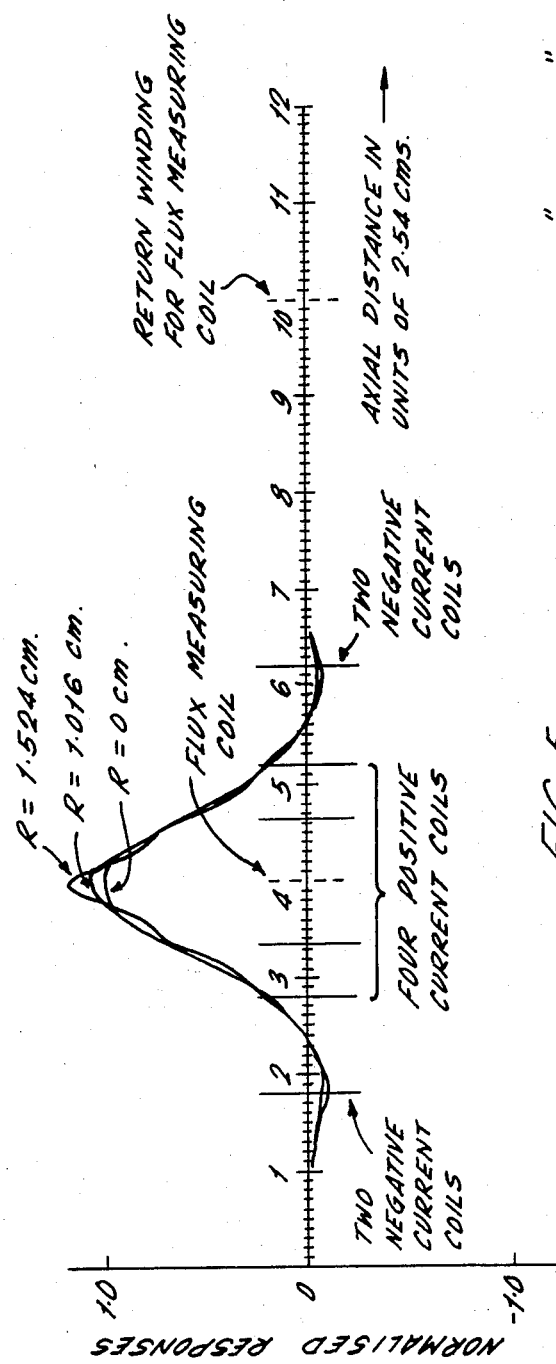

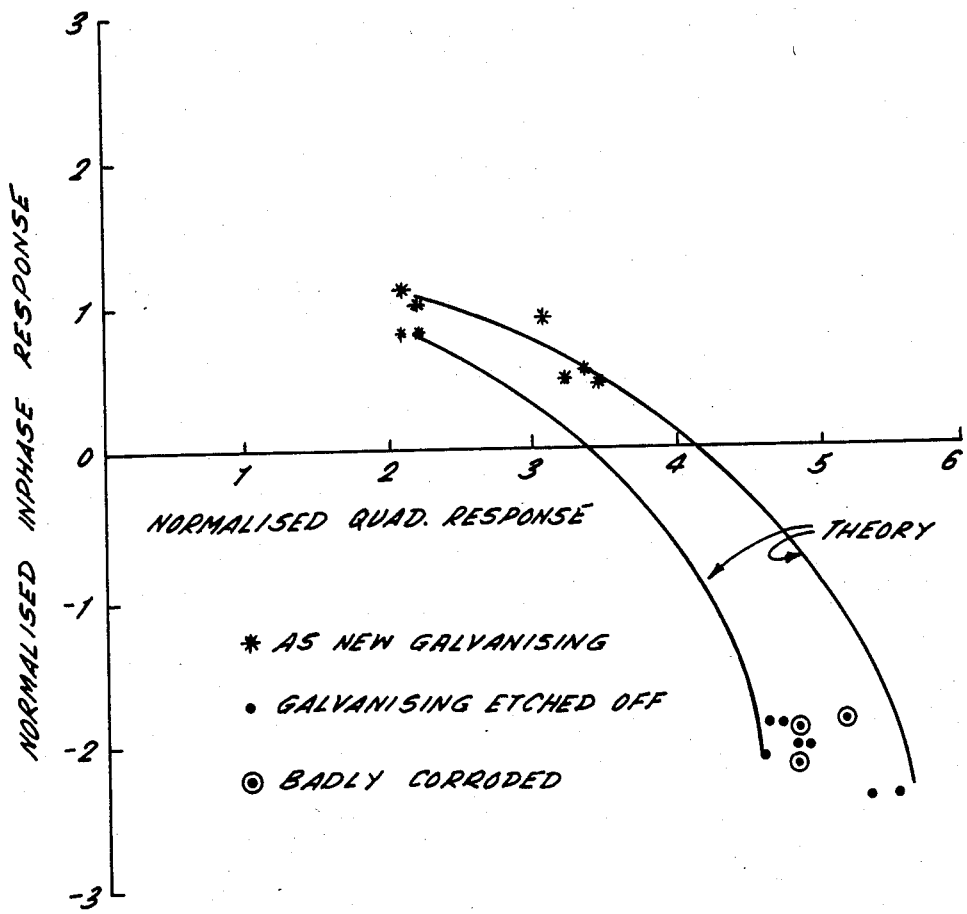
FIG. 6. NORMALISED RESPONSES FOR STEEL STRANDS.

APPARATUS FOR AND METHOD OF MONITORING THE CORROSION IN ELECTRICAL POWER CABLES BY MEASURING THE VARIATION IN INDUCED EDDY CURRENTS

BACKGROUND OF THE INVENTION

This invention relates to the monitoring of corrosion occuring to metal cables. Metal cables located in a hostile corrosive environment can be protected from corrosion by a variety of defences such as plastic cladding, grease or galvanising. For example, power cables mounted above ground comprise two or three layers of aluminum strands helically laid over a central core of seven galvanised steel strands. The steel core can also be greased. When moisture penetrates to the core of a cable wherein the grease layer is poor, through say use, the galvanised layer on the steel provides some protection. Eventually, however, the steel is exposed and the aluminium becomes anodic and subject to galvanic corrosion. Generally the severest corrosion then occurs on the inner aluminium strands and is invisible from exterior observation; therefore, detection of the corrosion is very difficult. Only in advance stages of this type of corrosion does bulging of the cable occur allowing visible detection. Although non-destructive tests such as infra-red scanning of energised lines can detect corrosion, the detection is only at the later stages of corrosion. During the process of corrosion both the electrical and mechanical properties of the cable are degraded and ultimately failure of the cable can occur.

SUMMARY OF THE INVENTION

It is an object of the invention to provide a metal cable corrosion monitor capable of detecting corrosion by examining magnetic field penetration into the cable. According to one aspect of the invention there is provided a metal cable corrosion monitor comprising a sensing head having application means capable, in use, of applying a magnetic field coaxially to a portion of cable to be monitored and detection means, defining a detection area encircling said portion, capable of detecting magnetic flux parallel with the cable and linking with the area and producing therefrom a signal containing information as to amplitude and phase parameters of the flux detected; the monitor also including a control means having means to activate said application means to apply an alternating field with a predetermined frequency and having means to receive said signal and to evaluate said parameters therefrom, the values of the parameters providing an indication of the corrosion of the cable portion monitored.

By employing the corrosion monitor in accordance with the invention it is possible to carry out nondestructive testing of the cables, testing which can detect the interior corrosion of a multi-strand cable being monitored. By observation of the amplitude and phase parameters of the flux detected it is possible to detect corrosion of a single or multi-strand cable and where the cable is a multi-strand cable having some strands comprising a second metal, it is possible to detect the preferential corrosion of the two metals since the amplitude parameter can comprise a response primarily derived from the first metal and the phase parameter can comprise a response primarily derived from the second metal.

In the cases when the cable includes a number of strands, it is preferable that the application means comprises a field winding having a line integral of magnetic field along the axis which is substantially zero. The effects of induced inter-strand currents can be reduced by a field winding comprising an inner winding flanked at each end by axially space coaxial outer windings each having half the number of turns as the inner winding, the field winding being split along its axis into two halves such that each half has semi-circular half turns, the field winding halves being hinged together at a hinge line and closing together along a closure line, the half turns being arranged in the field winding halves such that the windings of said field winding are formed by corresponding pairs of half turns in the two field winding halves, and with axial leads along the hinge and with closure lines interconnecting the half turns in each field winding half, whereby, in use, current flow in the outer windings has a reverse direction to current flow in the inner windings and current flow in adjacent axial leads, when the two field winding halves are closed, is equal and opposite, interconnection between the field winding halves being provided only at the hinge line. With this type of field winding, the sensing head can be clipped onto a cable to be monitored without the necessity for microconnectors to complete the turns of the field winding windings. The detection means can comprise a pick up coil located centrally within the inner winding.

The means to apply an alternating field is conveniently a power oscillator which also provides in phase and quadrature reference signals for the means to evaluate said parameters which preferably comprises two phase sensitive detectors. The predetermined frequency of the oscillating magnetic field preferably lies within the range from 50 KHz to 2 MHz. In order to detect specifically the effects of exclusion of flux from the cable encircled by the detection area the means to receive said signal includes a transformer arranged to provide a signal equal to and in anti-phase to that produced by the application means when no cable is encircled.

According to another aspect of the invention there is provided a field winding comprising an inner winding flanked at each end by axially spaced coaxially outer windings each having half the number of turns as the inner winding, the field winding being split along its axis into two halves such that each half has semicircular half turns, the field winding halves being hinged together at a hinge line and closing together along a closure line, the half turns being arranged in the field winding halves such that the said field winding windings are formed by corresponding pairs of half turns in the two field winding halves, and with axial leads along the hinge and closure lines interconnecting the half turns in each field winding half, whereby, in use, current flow in the outer windings has a reverse direction to current flow in the inner windings and current flow in adjacent axial leads, when the two field winding halves are closed, is equal and opposite, interconnection between the field winding halves being provided only at the hinge line.

BRIEF DESCRIPTION OF THE DRAWINGS

Examples of the present invention will now be described with reference to the accompanying drawings, in which:

FIG. 3. illustrates a response chart of the monitor for a metal conductor;

FIG. 4. illustrates computed axial magnetic fields for the sensing head shown in FIG. 2;

FIG. 5. illustrates computed incremental normalised responses for a pick-up coil employed with the sensing head shown in FIG. 2.

FIG. 6. illustrates a conductor response using the monitor shown in FIG. 1.

DESCRIPTION OF PREFERRED EMBODIMENTS

Figure 1:
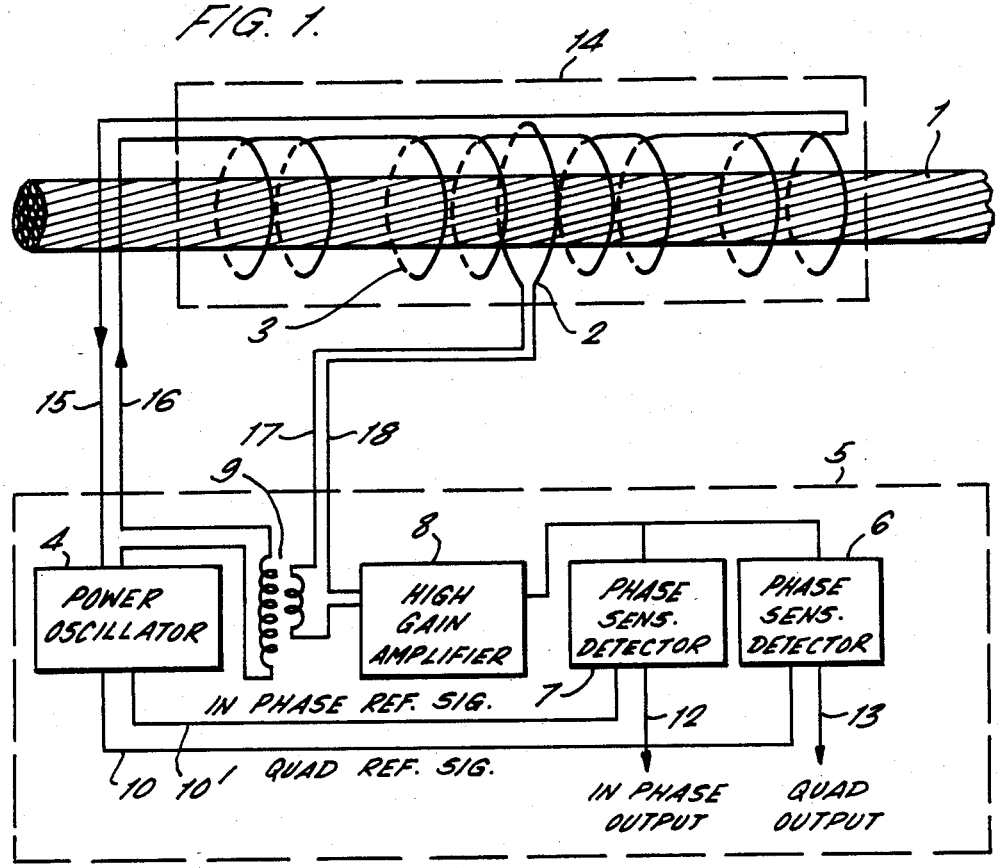
FIG. 1. illustrates a metal cable corrosion monitor embodying the invention.

A metal cable corrosion monitor embodying the invention comprises a magnetic field application field winding of radius R arranged to encircle a portion of a single strand cable to be monitored. When the solenoid is activated to produce a magnetic field $H'_s$ having an alternating frequency w, then the entry of the field into the conducting strand of the cable is inhibited to a skin depth $\delta$ by eddy currents. It is known that for a semi-infinite conducting slab the so called skin depth $\delta$ is given by $$\delta = \left( \frac{2p}{u_o \, \mu_r \, w} \right)^{\frac{1}{2}} \quad (1)$$

where P and $u_r$ are the restivity and relative permeability of the slab respectively and $\mu_o$ is the permeability of free space.

If an aluminium cable of a single strand radius r of 1.58 mm is monitored for example with a very high frequency, say 77 KHz, then $\delta$ is very much less that r, being equal to approximately 0.29 mm. The magnetic field produced by the field winding along the cable axis induces currents around the circumference of the cable which exclude the flux from the cable interior. If a flux measuring coil, for example a single turn pick-up coil also of radius R coaxial with the field winding, encircles the cable, then the r.m.s. output of the pick-up coil linking r.m.s. flux $\phi$ parallel with the cable axis is $$V = w\phi' = w\mu_o H'_s(\pi R^2 - \pi r^2) \quad (2)$$

Clearly the induced voltage $wu_o H'_s \pi R^2$ is not wanted and can be eliminated by employing an identical but opposing phase compensation voltage $V'_c$. Therefore the voltage from the pick-up coil is $$V_m = V - V_c = w\mu_o H'_s \pi r^2 \quad (3)$$

It will be apparent that when the field winding is empty $V'_m$ is zero and increases in proportion to the area of aluminium cable within it.

However there is some pentration of the flux into the cable. If the above equations are extended to include the pentration of the cable, then it will be apparent to a person skilled in the art that $$V_m = \mu_o w H'_s \pi r^2 \left[ \left(1 - \frac{\delta u_r}{r}\right) \sin wt + \frac{\delta u_r}{r} \cos wt \right] \quad (4)$$

where $H_s \cos wt$ represents the amplitude and phase of the field winding applied field. The sine term results from flux excluded from the cable and the (cos-sin) term is due to phase shifted flux pentrating the surface of the cable. By monitoring the amplitude of the sine term and or the phase shifted amplitude it is possible to detect the effects of corrosion on the cable.

Equation 4 shows markedly different responses for different metals. For example with new aluminium $\mu_r = 1$, therefore the measured voltage is largely due to flux exclusion and will be in phase with the compensation voltage. For steel however $\mu_r$ is high (typically 50 and 100 KHz). So even though $\delta$ is small, because the permeability is high, flux within the surfaces tends to be greater than that excluded. Thus steel produces a signal that is larger than that of aluminium but negative in phase signal with a positive quadrature. The effects of cable corrosion on the parameters of in phase and phase shifted amplitude can be evaluated theoretically and emperically, and subsequently observed values can then be compared with the emperically gained values in order to obtain an indication of the corrosion of the cable.

The above relates to single strand cable but can also be related to multi-strand cables. Clearly in a multi-strand cable wherein there is a central core say of steel enclosed within helically wound strands of aluminium, it is possible to determine the condition of the aluminium and steel strands and to distinguish between them. For example, if the in phase voltage is compared with a reference signal and is set to give maximum in phase signals with new aluminium strands, and the quadrature signal voltage is arranged to give a zero quadrature signal with new aluminium strands, the corrosion of the steel can be monitored. The phase of the reference signals required can be obtained by rewriting the equation 4 in the form $$V_m = (\mu_o w H'_s) \pi r^2 \, P \sin(wt + \epsilon) \quad (5)$$

$$P = \left[ \left(1 - \frac{\delta u_r}{r}\right)^2 + \left(\frac{\delta u_r}{r}\right)^2 \right]^{\frac{1}{2}} \quad (5a)$$

$$\epsilon = \tan^{-1}\left( \frac{r}{\delta u_r} - 1 \right) \quad (5b)$$

Therefore the phase of the reference signal to the in phase detected signal is advance by $\epsilon$ degrees (with respect to the compensation voltage) to give the required maximum signal from aluminium strands. The reference signal to the quadrature signal is shifted by 90° to give zero response with aluminium strands, a typical value for $\epsilon$ for aluminium is found to be 13°. Preferably an operating frequency of 1 MHz is employed for aluminium cable since this allows the detection of small losses in aluminium cross section due to corrosion.

In a cable wherein the above steel core comprises galvanised steel strands, the core strands are found to behave in a similar manner to aluminium. However a badly corroded strand gives a response similar to that of bare steel. FIG. 6 shows measured responses of the in-phase and quadrature parameters for some as new galvanised strands (*) and for these same strands after the galvanising was etched off with nitric acid (●). The responses from steel strands from an old cable suffering from severe sorrosion (⊙) are close to those of the bare strands. All the responses are normalised to the measured in phase response from a single aluminium strand. The scatter in the responses of the bare and badly corroded strands is due to variations in their permeabilities and electrical resitivities. The scatter of the responses of the galvanised strands is due mainly to the variations of the resistances of the galvanising layers, the thicknesses and restivities of which will vary. In spite of the scatter of measured responses in this figure, the as new galvanised and bare steel strands lie within two well defined zones and the separation between them is sufficient to give a clear indication of any corrosion.

It will be apparent therefore that the galvanized strands have an intermediate response between those of bare steel and aluminium strands. Therefore with a cable comprising a steel core made up of a galvanised steel surrounded by aluminium within helical layers, preferential corrosion can be monitored. The above described corrosion monitor employs a sensing head having a field application field winding arranged to encircle a section of a cable to be monitored. This is preferably employed for use on an isolated strand of cable or a group of strands electrically insulated from each other, by grease for example. However when the strands are in good electrical contact, the screening currents can tend to flow between strands right around the circumference of the cable, instead of being restricted to individual strands. Consequently misleading responses are given. Furthermore when the cable comprises a high permeability central core having a relatively lower permeability outer layer of conductors of different metal, the interlayer conduction is high. If the outer layer comprises oppositely wound helices, then interlayer conduction can be much greater than the inter strand conduction. This problem can be more acute when there are steel strands in the cable core. The interlayer conduction can be reduced by shortening the field winding to a length less than the pitch length of the outer layers which are wound about the central core. A field winding comprising a central region producing the main excitation field can have at each end a winding having half the number of turns as the main winding but wound in the opposite direction. Consequently the line integral of axial magnetic field along the field winding is substantially zero within, say, half a pitch length of the strand helix.

Therefore the net axial flux enclosed by the strand helices is greatly reduced and so are the interlayer voltages and currents. It has been found that this construction of field winding reduces the effects of the interlayer currents, and any limited sensitivity of the measured responses to inter strand currents can be beneficial, since it gives an indication of the inter strand resistance and hence whether, say, the strands are effectively greased or not. Further evaluation of the structure of the sensing head including the field winding can be achieved by computer aided design of the field winding and pick-up coil. The first step in the design involves evaluating the spatial response of a strand due to unit current in the field winding. Individual contributions from each of the individual turns can be calculated by use of the appropriate field equations. Consequently the axial field $H_{SD}$ induces currents around the surface of a single strand cable to be monitored.

Considering surface screening currents at high frequency, a current of amplitude.

$$\Delta I_S = -H_D \Delta x$$

is induced around the surface of the strand to cancel the field inside it, where $\Delta x$ is an element of length of the strand. The second step is to evaluate the flux linking the pick-up coil due to unit current in the strand element.

From mutual inductance considerations it follows that this flux is the same as that linking the strand element due to unit current in the pick-up coil. This flux is equal to the product of the field, $\mu_o H_{SP}$, at the strand element due to unit current in the pick up coil and the strand area $\pi r^2$. The induced voltage due to the strand element $\Delta x$ is thus $$V = \mu_o w \pi r^2 H_{SD} H_{SP} \Delta x.$$

The total induced voltage from a long strand can be obtained by numerical integration of many elements along the strand.

By employing a suitable computer programme to cope with sensing heads having many coaxial currents and pick-up coils of any radius, a near optimum sensing head design can be achieved. The sensing head parameters and incremental responses are shown in FIG. 5, in which the coil dimensions are given in inches for convenience, although any unit dimension can be employed. The driving coil has four positive turns in the central winding, with a large gap around the central pick-up coil. There is a pair of negative turns on either side of the central region, and the return winding for the pick-up coil is remote from the driving coil. These curves show the local responses for short strand elements as a function of axial position at three different radial positions. The local responses were summed to give the total responses for long strands, and the tabulated values were found to be unchanged, provided more than 100 elements are used in the summation. The total responses for this design are constant to within $+$ and $-1.5\%$ for radial positions up to 0.6" from the axis. The sensing head as shown can detect even very short defects in the conductor, since over 96% of the total response is due to the conductor within an axial distance of $+$ and $-1"$ of the central pick-up coil. The computed changes of local axial magnetic fields are shown in FIG. 4. The dip in the axial field at the centre of the winding compensates for the increased coupling between the central pick-up coil.

FIG. 1 illustrates a metal cable corrosion monitor embodying the invention. A section of a cable 1, the corrosion of which is to be monitored, is surrounded by a sensing head 14. The cable head includes a field winding comprising four central winding turns around the the cable having current flow in a first direction, flanked at either end by two winding turns respectively around the coil cable having current flowing in a direction the reverse of that flowing in the central turns. The winding 3 is connected via lines 15 and 16 to a power oscillator 4 which provides a known current to the windings at a predetermined frequency.

A pick up coil 2 is located in the centre of the central four turns of the field winding, as described herein above, so that its detection area encloses the cable and can detect the magnetic flux parallel to the cable axis and linking the area of the pick-up coil. The coil 2 is connected via lines 17 and 18 to a high gain amplifier 8. The above described return winding for the pick-up coil is not shown for the purposes of clarity. The line 17 is connected through the secondary windings of a transformer 9 before being connected to the amplifier 8. The secondary winding of transformer 9 therefore provides the anti-phase composition voltage to remove the value $V'_c$ shown in equation 3. In this way the response of the pick-up coil is zero volts when no cable is within the field winding.

The output of the amplifier 8 is relayed to a first phase sensitive detector 7 and a second phase sensitive detector 6. These phase sensitive detectors 6 and 7 receive reference signals from the oscillator 4 on lines 10 and 10' respectively relating to a quadrature reference signal and an in phase reference signal respectively, the phases of which can be adjusted to have the correct phase relative to the compensation voltage. The DC voltage outputs of the phase sensitive detectors 6 and 7, produced on lines 12 and 13 respectively, give an indication of the corrosion of the of the cable. The values can be analysed and are proportional to the phase quadruture component and the amplitude of the signal in phase with the reference signal respectively and can be equated with the relevant components from equation 4.

Ideally the monitor characterises cables as new by a unique pair of values of the in phase and quadruture voltages, and any deviation from these values indicates the precise nature and extent of any corrosion. Naturally the accuracy of the monitor is reduced by variations in the properties of the cable. For example, a galvanised steel core having helical outer bands of aluminium strands gives considerable scatter in responses as a result of permitted tolerances in the lay angles of the aluminium strands and in their diameters. FIG. 3 illustrates a response chart for such a cable and also shows the response band of uncorroded conductors with low inter strand resistance. The large in phase voltage results from currents flowing between the aluminium strands if they are clean or well greased. The position of the response in this band is also determined by the tension of the cable which, because of the helical layer of outer strands, produces radial pressure and reduces resistance between strands. By employing the above described sensing head wherein there is a low net axial flux, inter strand currents are reduced if there is no internal corrosion, and are insignificant for corroded conductors, so there is no extra broadening of responses. Hence inter strand currents tend to accentuate the differences in responses between uncorroded and corroded conductors and could help indicate whether the aluminium strands are greased. FIG. 3 illustrates that there is adequate separation between the uncorroded and fully corroded responses to give an ambiguous indication of significant internal corrosion. Internal corrosion is usually sporadic along a cable with sections not having significant corrosion. Thus most of the cable monitored would give a constant response representative of its as new condition and so defining more precisely the position of uncorroded response than the broad band of FIG. 3.

Figure 2:
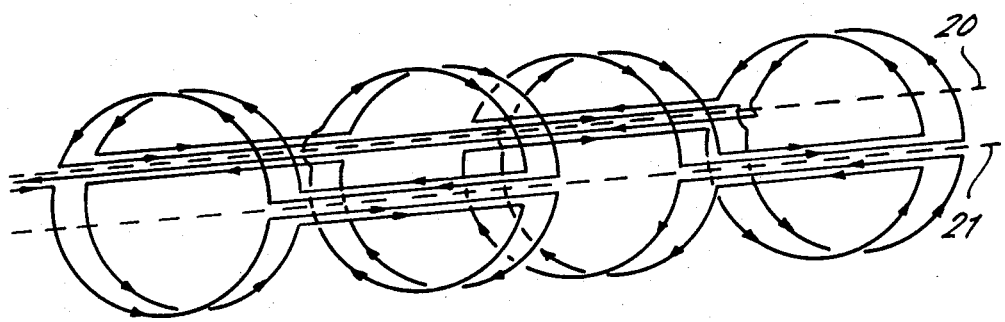
FIG. 2. illustrates a sensing head for use with a monitor in accordance with the invention.

The above mentioned frequency of 77 kHz can be used for monitoring a cable comprising a galvanised steel core having outer aluminium strands. Another operating frequency for detection of corrosion of individual or multi-strand aluminium cable would be 1 MHz. More particularly, referring to FIG. 2 the sensing head is formed such that it can be separated into two halves hinged along a hinge line 20 and can be clipped over a cable to be monitored to close along a closure line 21. By employing the fact that the sensing head includes an inner winding flanked at each end by axially spaced coaxial outer windings each having half the number of turns as the inner winding, it is possible to form a sensing head wherein the field winding is split along its axis into two halves and interconnection between the field winding halves is provided only at the hinge line. The field winding is split along its axis into the two halves such that each half has semi circular half turns, and the half turns are arranged in the field winding halves as illustrated in FIG. 2 such that the field winding windings are formed by corresponding pairs of half turns in the two solenoid halves. Axial leads along the hinge and closure lines interconnect the half turns in each field winding half so that current flow in the outer windings has a reverse direction to current flow in the inner windings. The leads can be arranged, as illustrated in the figure, so that current flow in adjacent axial leads, when the two field winding halves are closed, is equal and opposite, thereby substantially cancelling the effects of magnetic fields from the current flow in the axial lead. In this way a simple and convenient form of field winding suitable for the sensing head is formed. The same arrangement can be used for the pick-up coils with the return winding located well away from the drive windings comprising the inner windings of the field winding. This form of field winding allows the sensing head to have a very rugged clip-on form and to be constructed without any electrical connectors. The metal corrosion monitor embodying the invention can be run from batteries and can include a display screen having a response chart attached to the screen to facilitate interpretation of the monitored voltages. Clearly the monitor could also be mounted on mobile equipment such that a cable is automatically monitored along its length and the evaluated parameters transmitted to a central control or automatic data recorder.

It will be apparent that the field winding can be constructed so that there is only one connection across the hinge line of the field winding halves. Furthermore the frequency range for the field winding employed in the monitor is limited only in dependence on the cable to be monitored. An optimum frequency for most usual cables encountered is from 50 kHz to 2 MHz. Therefore the metal corrosion monitor in accordance with the invention can monitor single strand metal cable, multi-strand metal cable and mixed metal multi-strand cable.

I claim:

1. Apparatus for monitoring corrosion in electrical power cables of the kind having a galvanised steel core surrounded by a plurality of helically wound aluminium strand layers with adjacent aluminium strand layers being wound in opposite directions, the apparatus comprising:

a sensing head adapted to be applied to a cable to be monitored and including a field winding coaxially embracing the cable when the sensing head is applied thereto and to apply a magnetic field to a predetermined length of the cable, the field winding having an excitation portion, for applying over a test part of said cable length a field which is coaxial to the cable, and at least one return portion axially spaced from said excitation portion, for applying a field opposite to said coaxial field of the excitation portion, whereby the line integral of the axial magnetic field applied by the field winding over said cable length is zero, and a sense winding having a fixed diameter and located relative to the field winding to surround said test part of said cable length;

means for energising said field winding to produce an applied alternating magnetic field at a predetermined frequency at which the applied field is substantially excluded from the aluminium strands; and receiving means for detecting a voltage induced in the sense winding by magnetic flux linking with said sense winding, said receiving means arranged to evaluate both the amplitude of the induced voltage and the phase thereof relative to the applied alternating magnetic field.

2. An apparatus as claimed in claim 1, wherein said predetermined frequency is above a lower limit of 50 KHz and below an upper limit of 2 MHz.

3. An apparatus as claimed in claim 1, wherein the field winding comprises an excitation portion; a pair of axially spaced return portions positioned to flank each end of the excitation portion, each return portion having half the number of turns as the excitation portion, the field winding being split along its axis into two halves such that each half has semi-circular half turns, hinging means hinging the field winding halves together at a hinge line and permitting the field winding halves to close together along a closure line, the half turns being arranged in the field winding halves such that the winding of the field winding are formed by corresponding pairs of half turns in the two field winding halves with axial leads along the hinge and closure lines interconnecting the half turns in each field winding half, interconnection between the field winding halves being provided only at the hinge line; whereby current flow in the return portions has a reverse direction to current flow in the excitation portion and current flow in adjacent axial leads, when the two field winding halves are closed, is equal and opposite.

4. An apparatus as claimed in claim 1, wherein the sense winding includes a flux measuring coil located centrally within the excitation portion.

5. An apparatus as claimed in claim 1 wherein the means for energising said field windings comprises a power oscillator also providing in phase and quadrature reference signals for the receiving means.

6. An apparatus as claimed in claim 5 wherein the receiving means comprises phase sensitive detectors.

7. An apparatus as claimed in claim 6 wherein the power oscillator provides the in-phase reference signal phase shifted to indicate a maximum magnitude of induced voltage for uncorroded cables.

8. An apparatus as claimed in claim 1 wherein the receiving means includes a transformer arranged to provide a signal equal to and in anti-phase to that produced when no cable is encircled.

9. A field winding for applying a magnetic field to a predetermined length of electric power cable comprising:

an excitation portion for applying over a test part of a cable length a field which is co-axial with the cable;

a pair of axially spaced co-axial return portions flanking the excitation portion at each end thereof, each return portion having half the number of turns as the excitation portion;

the field winding being split along its axis into two halves such that each half has semi-circular half turns;

hinging means hinging the field winding halves together at a hinge line and permitting the field winding halves to close together along a closure line, the half turns being arranged in the field winding halves such that the windings of said field winding are formed by corresponding pairs of half turns in the two field winding halves with axis leads along the hinge and closure lines interconnecting the half turns in each field winding half, interconnection between the field winding halves being provided only at the hinge line;

whereby current flow in the return portions has a reverse direction to current flow in the excitation portion and current flow in adjacent axial leads, when the two field winding halves are closed, is equal and opposite so that the line integral of the axial magnetic field applied by the field winding over said cable length is zero.

10. A method for monitoring corrosion in electrical power cables of the kind having a galvanised ferromagnetic core surrounded by a plurality of helically wound aluminium strand layers with adjacent strand layers being wound in opposite directions, the method comprising the steps of:

applying an alternating magnetic field to a predetermined length of the cable, said applied field including a first field portion which is coaxial over a test part of the cable and a second field portion opposite to said first field portion over at least one part of the cable axially spaced from said test part, whereby the line integral of the applied axial alternating magnetic field over said predetermined length is zero, the alternating field being of a frequency at which it is substantially excluded from the aluminium strands;

sensing the axial magnetic field at said test part both in and excluded from the cable; and evaluating both the amplitude and phase of the sensed field to detect the presence of corrosion in the cable.

* * * * *

UNITED STATES PATENT AND TRADEMARK OFFICE
CERTIFICATE OF CORRECTION

PATENT NO. : 4,652,823
DATED : March 24, 1987
INVENTOR(S) : John SUTTON

It is certified that error appears in the above—identified patent and that said Letters Patent is hereby corrected as shown below:

Column 3, in equation (1) change "$u_o$" to -- $\mu_o$ --.
Column 3, line 30, change "P" to -- p --.
Column 3, line 30, change "$u_r$" to -- $\mu_r$ --.
Column 3, line 47, change "$u_o$" to -- $\mu_o$ --.
Column 3, in equation (4) change "$H_s^1$" to -- $H_s$ --, and change "$u_r$" (two places) to -- $\mu_r$ --.
Column 4, line 10, change "and" to -- at --.
Column 4, line 17, change "emperically" to -- empirically --.
Column 4, line 18, change "emperically" to -- empirically --.
Column 4, in equation (5a) change "$u_r$" (two places) to -- $\mu_r$ --.
Column 4, in equation (5b) change "$u_r$" to -- $\mu_r$ --.
Column 4, line 67, change "sorrosion" to -- corrosion --:
Column 7, line 2, change "composition" to -- compensation --.
Column 7, line 16, change "of the of the" to -- of the --.
Column 7, lines 49 and 50, change "ambiguous" to -- unambiguous --.

Signed and Sealed this

Fifteenth Day of September, 1987

Attest:

DONALD J. QUIGG

Attesting Officer  Commissioner of Patents and Trademarks